United States Patent [19]
Rogers

[11] Patent Number: 5,886,208
[45] Date of Patent: *Mar. 23, 1999

[54] SUBSTITUTED B-AMINO ACID DERIVATIVES USEFUL AS PLATELET AGGREGATION INHIBITORS

[75] Inventor: Thomas Edward Rogers, Ballwin, Mo.

[73] Assignee: G. D. Searle & Co., Chicago, Ill.

[ * ] Notice: The term of this patent shall not extend beyond the expiration date of Pat. No. 5,344,957.

[21] Appl. No.: 835,598

[22] Filed: Apr. 10, 1997

Related U.S. Application Data

[60] Division of Ser. No. 452,621, May 25, 1995, Pat. No. 5,625,093, which is a continuation-in-part of Ser. No. 221,913, Apr. 1, 1994, abandoned, which is a division of Ser. No. 953,601, Oct. 6, 1992, Pat. No. 5,344,957, which is a continuation-in-part of Ser. No. 866,933, Apr. 10, 1992, Pat. No. 5,239,113, which is a continuation-in-part of Ser. No. 777,811, Oct. 15, 1991, abandoned.

[51] Int. Cl.[6] .................................................. C07C 229/34
[52] U.S. Cl. .............................................. 560/35; 562/440
[58] Field of Search ................................. 560/35; 562/440

[56] References Cited

U.S. PATENT DOCUMENTS

| | | | |
|---|---|---|---|
| 3,862,228 | 1/1975 | Rodriguez et al. | 560/13 |
| 4,517,686 | 5/1985 | Ruoslathi et al. | 623/11 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,857,508 | 8/1989 | Adams et al. | 514/18 |
| 4,879,313 | 11/1989 | Tjoeng et al. | 514/616 |
| 5,039,805 | 8/1991 | Alig et al. | 562/430 |
| 5,053,393 | 10/1991 | Tjoeng et al. | 564/153 |
| 5,084,466 | 1/1992 | Alig et al. | 514/353 |
| 5,086,069 | 2/1992 | Klein et al. | 562/439 |
| 5,220,050 | 6/1993 | Bovy et al. | 514/357 |
| 5,239,113 | 8/1993 | Bovy et al. | 562/440 |
| 5,254,573 | 10/1993 | Bovy et al. | 562/430 |
| 5,272,162 | 12/1993 | Tjoeng et al. | 514/344 |
| 5,273,982 | 12/1993 | Alig et al. | 514/315 |
| 5,378,727 | 1/1995 | Bovy et al. | 562/430 |

FOREIGN PATENT DOCUMENTS

| | | |
|---|---|---|
| 298820 | 6/1987 | European Pat. Off. . |
| 275748 | 7/1988 | European Pat. Off. . |
| 372486 | 10/1989 | European Pat. Off. . |
| 381033 | 11/1989 | European Pat. Off. . |
| 445796 | 3/1990 | European Pat. Off. . |

OTHER PUBLICATIONS

Koczewiak et al. Biochem., 23, 1767–1774 (1984).
Plow et al. Proc. Natl. Acad. Sci., 82, 8057–8061 (1985).
Ruggieri et al. Proc. Natl. Acad. Sci., 83, 5708–5712 (1986).
Haverstick et al. Blood, 66(4), 946–952 (1985).
Ruoslahti et al. Science, 238, 491–497 (1987).
Boere et al. J. Organomet. Chem., 331, 161–167 (1987).
Parham et al. Acct. Chem. Res., 300, (1982).
Taddei et al. Synthesis, 633–635 (1986).
Allen et al. Org. Synth. Coll., vol. 2, 3 140 (1955).
Ginsberg et al. J. Biol. Chem., 260 (7), 3931–3936 (1985).

*Primary Examiner*—Paul J. Killos
*Attorney, Agent, or Firm*—Cynthia S. Kovacevic

[57] ABSTRACT

Novel substituted amino acid derivatives are provided which inhibit platelet aggregation and which are useful in pharmaceutical compositions and methods of inhibiting platelet aggregation.

14 Claims, No Drawings

SUBSTITUTED B-AMINO ACID DERIVATIVES USEFUL AS PLATELET AGGREGATION INHIBITORS

This is a DIVISIONAL Application of application Ser. No. 08/452,621, filed on May 25, 1995, now U.S. Pat. No. 5,625,073, which is a CONTINUATION-IN-PART of 08/221,913, filed on Apr. 1, 1994, abandoned, which is a DIVISIONAL OF 07/953,601, filed on Oct. 6, 1992 (U.S. Pat. No. 5,344,957), which is a CONTINUATION-IN-PART of 07/866,933, filed on Apr. 10, 1992 (U.S. Pat. No. 5,239,113), which is a CONTINUATION-IN-PART of 07/777,811, filed Oct. 15, 1991, which is ABANDONED.

FIELD OF THE INVENTION

This invention pertains to substituted β amino acid derivatives which inhibit platelet aggregation.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating platelet thrombus formation.

It is also known that another large glycoprotein named fibronectin, possesses cell-attachment properties. Various relatively large polypeptide fragments in the cell-binding domain of fibronectin have been found to have cell-attachment activity. (See U.S. Pat. Nos. 4,517,686; 4,589,881; and 4,661,111). Certain relatively short peptide fragments from the same molecule were found to promote cell attachment when immobilized on the substrate or to inhibit attachment when in a solubilized or suspended form. (See U.S. Pat. Nos. 4,578,079 and 4,614,517).

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., Ibid. 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

U.S. Pat. No. 4,879,313 discloses compounds useful as inhibitors of platelet aggregation having the formula:

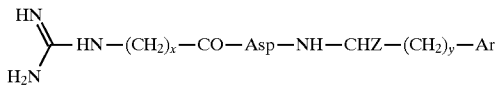

wherein
x=6 to 10,
y=0 to 4,
z=H, COOH, CONH2 or Cl-6 alkyl,
Ar=phenyl, biphenyl or naphthyl, each substituted with 1 to 3 methoxy groups, or an unsubstituted phenyl, biphenyl, naphthyl, pyridyl or thienyl group, and
Asp=aspartic acid residue.

European Patent Application 372,486 discloses N-acyl β amino acid derivatives of the formula:

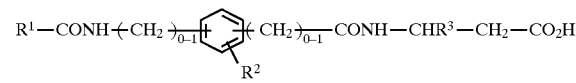

and their salts. Said compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

European Patent Application 445,796 discloses acetic acid derivatives which have inhibitory action on the bonding of adhesive proteins to blood platelets as well as on blood platelet aggregation and cell-cell adhesion.

European Patent Application 372,486 discloses N-acyl beta amino acid derivatives and their salts. Said compounds are useful for inhibiting platelet aggregation in the treatment of thrombosis, stroke, myocardial infarction, inflammation and arteriosclerosis and for inhibiting metastasis.

SUMMARY OF THE INVENTION

In accordance with the present invention novel substituted β amino acid derivatives are provided which modulate and/or inhibit platelet aggregation. These novel inhibitor compounds can be represented by the following chemical Formula I

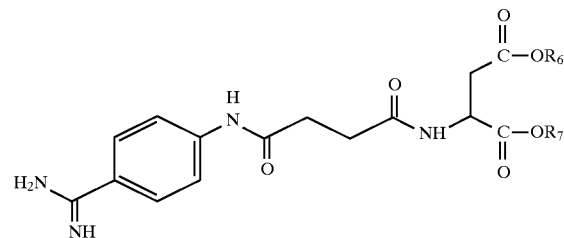

or pharmaceutically acceptable salts thereof,
wherein $R_6$ and $R_7$ are independently selected from the group consisting of hydrogen, lower alkyl radicals, lower alkenyl radicals, aromatic hydrocarbon radicals, alicyclic hydrocarbon radicals, and arylalkyl radicals wherein the radicals are optionally substituted.

It is another object of the invention to provide pharmaceutical compositions comprising at least one compound of the Formula I which compositions are useful in inhibiting or modulating platelet aggregation.

It is still another object of the invention to provide a method for inhibiting or modulating platelet aggregation in a mammal in need of such treatment comprising administering a compound of the Formula I.

DETAILED DESCRIPTION OF THE INVENTION

The present invention is directed to compounds of the Formula I:

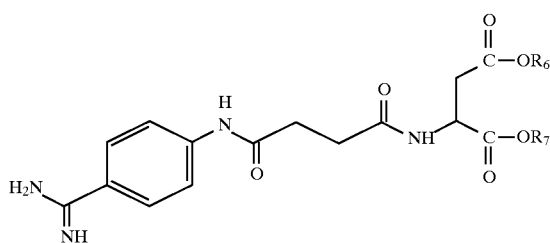

or pharmaceutically acceptable salts thereof,
wherein $R_6$ and $R_7$ are independently selected from the group consisting of hydrogen, lower alkyl radicals, lower alkenyl radicals, aromatic hydrocarbon radicals, alicyclic hydrocarbon radicals, and arylalkyl radicals, wherein the radicals are optionally substituted.

Exemplifying the invention are the following compounds:
2S-[[4-[[4-(aminoiminomethyl)phenyl]amino]-1,4-dioxobutyl]amino]butanoic acid;
N-[4-[[4-(aminoiminomethyl)phenyl]amino]-1,4-dioxobutyl]aspartic acid, 4-(1,1-dimethylethyl)ester;
N-[4-[[4-(aminoiminomethyl)phenyl]amino]-1,4-dioxobutyl]aspartic acid, 4-(phenylmethyl)ester;
N-[4-[[4-(aminoiminomethyl)phenyl]amino]-1,4-dioxobutyl]aspartic acid, 4-methyl ester;
N-[4-[[4-(aminoiminomethyl)phenyl]amino]-1,4-dioxobutyl]aspartic acid, 4-ethyl ester;
N-[4-[[4-(aminoiminomethyl)phenyl]amino]-1,4-dioxobutyl]aspartic acid, 4-(3-propenyl)ester;
N-[4-[[4-(aminoiminomethyl)phenyl]amino]-4-dioxobutyl]aspartic acid, 1-(1,1-dimethylethyl)ester; and
N-[4-[[4-(aminoiminomethyl)phenyl]amino]-1,4-dioxobutyl]aspartic acid, 1-phenylmethyl ester.

As utilized herein, the term "lower alkyl" alone or in combination, means an acyclic straight or branched hydrocarbon radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical containing at least one double bond. Such radicals contain from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "alicyclic hydrocarbon radical" or "cycloalkyl" means a cyclic hydrocarbon radical which is saturated or unsaturated containing 3 to about 10 carbon atoms, and preferably from 3 to about 6 carbon atoms. Examples of suitable alicyclic hydrocarbon radicals include cyclopropyl, cyclopropylenyl, cyclobutyl, cyclopentyl, cyclohexyl, 2-cyclohexen-1-ylenyl, cyclohexenyl and the like.

The term "aromatic hydrocarbon radical" or "aryl" as used herein means an aromatic carbon ring system composed of one or more aromatic rings which system contains 4 to about 16 carbon atoms, preferably 6 to about 12 carbon atoms, and more preferably 6 to about 10 carbon atoms. Examples of suitable aromatic hydrocarbon radicals include phenyl, naphthyl, biphenyl and the like.

The term "alkoxy", alone or in combination, means an alkyl ether radical wherein the term alkyl is as defined above and most preferably containing 1 to about 4 carbon atoms.

Examples of suitable alkyl ether radicals include methoxy, ethoxy, n-propoxy, isopropoxy, n-butoxy, iso-butoxy, sec-butoxy, tert-butoxy and the like.

The term "arylalkyl radical" as used herein refers to a lower alkyl radical, as defined above substituted by an aryl as defined above. Benzyl and phenylethyl are examples of such "arylalkyl radicals".

The term "optionally substituted radicals" as used herein means each of the above described radicals optionally substituted by groups such as alkyl, alkoxy, hydroxy, halo, amino, nitro, cyano, carbonyl and the like.

The term "pharmaceutically acceptable salt" refers to a salt prepared by contacting a compound of formula I, with an acid whose anion is generally considered suitable for human consumption. Examples of pharmacologically acceptable salts include the hydrochloride, hydrobromide, hydroiodide, sulfate, phosphate, acetate, propionate, lactate, maleate, oxalate, malate, succinate, and tartrate and citrate salts. All of these salts may be prepared by conventional means by reacting, for example, the appropriate acid with the corresponding compound of Formula I.

Suitable pharmaceutically-acceptable base addition salts of compounds of Formula I, include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine.

The compounds of the present invention may be administered by any suitable route, preferably in the form of a pharmaceutical composition adapted to such a route and in a dose effective for the treatment intended. Therapeutically effective doses of the compounds of the present invention required to treat or arrest progress of the medical condition are readily ascertained by one of ordinary skill in the art.

Total daily dose administered to a host in single or divided doses may be in amounts, for example, from 0.001 to 100 mg/kg body weight daily and more usually 0.01 to 10 mg/kg and most preferably 3 mg/kg. Dosage unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional pharmaceutically acceptable carriers, adjuvants, and vehicles.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are, conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more active pharmaceutical agents. When administered as a combination, the therapeutic agents can be formulated as separate compositions which are given at the same time or different times, or the therapeutic agents can be given as a single composition.

In the structures and formulas herein, the bond drawn across a bond of a ring can be to any available atom on the ring.

The compounds in this invention can exist in various isomeric forms and all such isomeric forms are meant to be included. Tautomeric forms are also included in the invention. Pharmaceutically acceptable salts of such isomers and tautomers are meant to be included as well.

The compounds of the present invention may be prepared by standard synthetic methods combined with methods analogous to solution phase peptide synthesis [see: The Peptides: Analysis, Synthesis, Biology (E. Gross and J. Meienhofer, eds.), Vol. 1–5, Academic Press, New York)].

Five general synthetic sequences are outlined in Schemes I–V.

SCHEME I

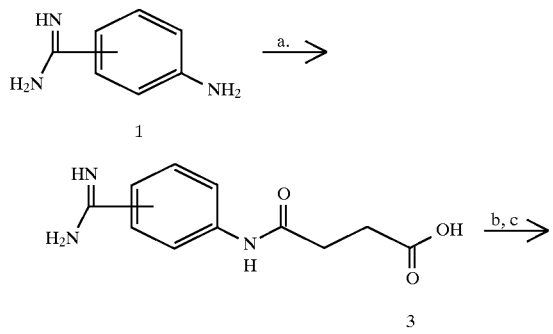

-continued
SCHEME I

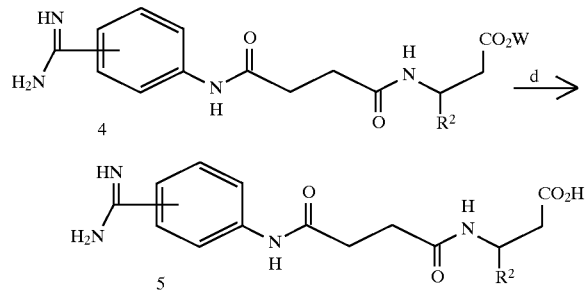

a. Succinic anhydride (2), pyridine, DMAP. b. i-BuOCOCl, NMM. c. β-Alanine derivative. d. NaOH or LiOH.

Wherein

W is selected from the group consisting of hydrogen, lower alkyl radicals, lower alkenyl radicals, lower alkynyl radicals, alicyclic hydrocarbon radicals and aromatic hydrocarbon radicals, wherein said radicals are optionally substituted with hydroxyl, lower alkoxy, lower alkyl, halogen, nitro, amino, acyloxy, and phenyl and naphthyl which may be optionally substituted with halogen, nitro, lower alkoxy, and lower alkyl; and $R_2$ is selected from the group consisting of hydrogen, lower alkyl radicals of 1 to about 6 carbon atoms, lower alkenyl radicals of 2 to about 6 carbon atoms, and lower alkynyl radicals of 2 to about 8 carbon atoms, alicyclic hydrocarbon radicals of 3 to 6 carbon atoms, aromatic hydrocarbon radicals; wherein said radicals are optionally substituted with hydroxyl, lower alkoxy, lower alkyl, halogen, nitro, cyano, azido, ureido, ureylene, amino, trialkylsilyl, alkylsulfonyl, phenylsulfonyl, trifluoromethyl, acetoxy, acetylamino, and benzoylamino; carbonyl, carboxyl derivatives, alkylsulfonyl amino, and phenylsulfonyl amino.

In Scheme I. The aminobenzamidine 1 (i.e., Z is hydrogen) is coupled to an alkanoic, alkenoic (both substituted or not) or alkynoic diacid. An activated form of the diacid is preferentially used. These activated forms include anhydrides, internal anhydride, acid chloride or one of the various activated forms as described in *Principles of Peptide Synthesis*, Bodansky, 1984, Springer-Verlag, the disclosure of which is hereby incorporated by reference. A highly preferred procedure involves condensation of an anhydride (e.g., succinic anhydride 2) with a salt of aminobenzamidine 1. The reaction is best conducted in a polar solvent such as methylene chloride, acetonitrile, dioxane, dimethylformamide, dimethylsulfoxide or a mixture of such solvents in the presence of an acid binding agent such as sodium, potassium or cesium carbonate, triethylamine, pyridine, sodium hydride, dimethylaminopyridine, diazabicycloundecene, or a mixture of such agents, at temperatures ranging between 0° C. and 120° C. The final compounds are obtained by coupling of the amidine derivative 3 with a properly protected aminoacid. The amide bonds are formed using standard coupling reagents, e.g., dicyclohexylcarbodiimide (DCC), carbonyldiimidazole (CDI), disuccinimidyl carbonate (DSC), benzotriazol-1-yl-oxy-tris (dimethylamino)phosphonium hexafluorophosphate (BOP) or isobutyl chloroformate (mixed anhydride method). When the amino acid used in the coupling was protected as an ester of the carboxylic acid function (4, W=alkyl, aryl, . . . ), the free acids 5 are obtained by a suitable deprotection method as described by T. H. Greene in *"Protective Group in Organic Synthesis"*, Wiley-Interscience, 1980, the disclosure of which is hereby incorporated by reference.

aminoacid. The amide bonds are formed using standard coupling reagents as described above for Scheme I.

SCHEME II

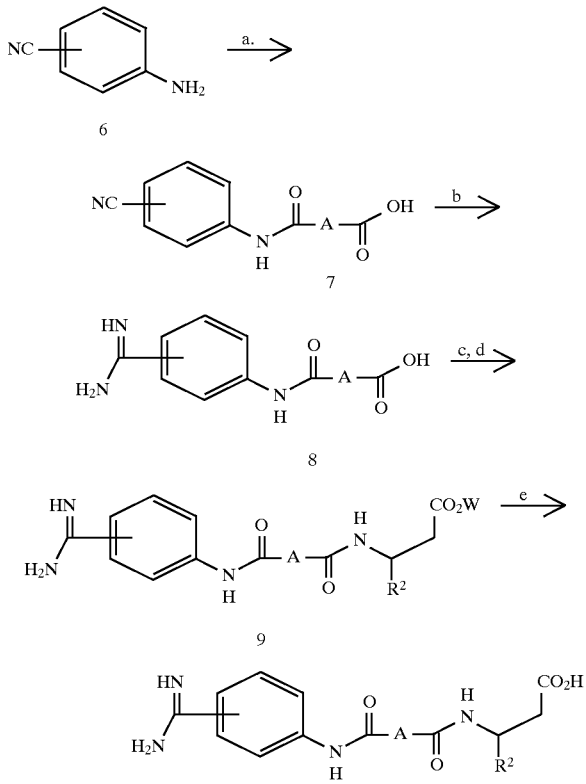

a. Activated diacid. b. H$_2$S, pyridine; MeI, acetone; NH$_4$AcO or hexamethyl disilazane in diethyl ether. c. Anhydride.
d. β-Alanine derivative. e. Base or acid.

W and R$^2$ have the values described in Scheme I and
A is selected from the group consisting of lower alkyl radicals, lower alkenyl radicals, lower alkynyl radicals and alicyclic radicals, wherein said radicals are optionally substituted with hydroxy, lower alkoxy, lower alkyl, halogen, alkoxycarbonylalkyl, amino, alkylamino, dialkylamino, acylamino, alkylthio, sulfonyl and aromatic hydrocarbons which are optionally substituted with halogen, nitro, lower alkoxy and lower alkyl.

Alternatively, an aminobenzonitrile 6, can be used for condensation with the desired diacid or diacid derivative. In that case, the nitrile can be converted to the amidine directly or at a later stage. When the aminobenzonitrile is used in the condensation reaction (Scheme II), the cyano group of the resulting intermediate 7 is converted to the amidine 8 via the thioimidate in nearly quantitative yield. The thioimidate is formed by first treating the cyano compound with hydrogen sulfide (H$_2$S) followed by alkylation with methyl iodide. Next, treatment of the thioimidate with ammonium acetate affords the amidine as the salt (HI). Alternatively, the nitrile 7 can be converted to the amidine 8 by the use of lithium bis(trimethylsilyl)amide in an inert solvent such as diethyl ether [R. T. Boere et al, *J. Organomet. Chem.*, 331, 161–67, (1987)], the disclosure of which is hereby incorporated by reference. The desired compounds are obtained by coupling of the amidine derivative 8 with a properly functionalized

SCHEME III

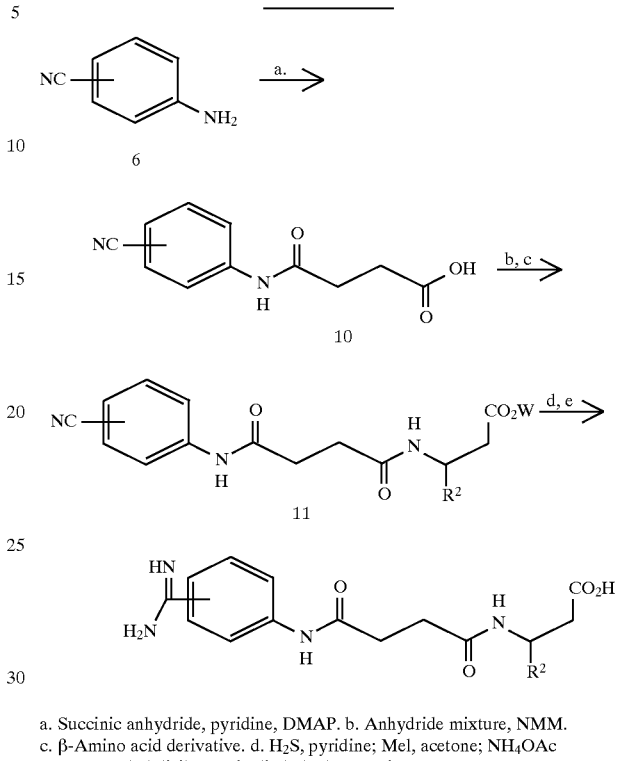

a. Succinic anhydride, pyridine, DMAP. b. Anhydride mixture, NMM.
c. β-Amino acid derivative. d. H$_2$S, pyridine; MeI, acetone; NH$_4$OAc or Hexamethyl disilazane in diethyl ether. e. LiOH or NaOH.

Scheme III illustrates the preparation of derivatives using the amino nitriles as reagents. The cyano group is kept unchanged as a precursor for the amidine function throughout two amide bond forming steps. The first intermediate 10 is directly engaged in a reaction with the desired amino acid. The intermediate 10 is then converted to the benzamidine. A method of choice to produce the amidine function is via the thioimidate procedure as described in Scheme II. It is desirable, in Scheme III, to prepare the intermediate 11 as an ester. The most desirable ester is the t-butyl ester which can be deprotected to the acid by contact with a strong acidic medium as HBr/AcOH or trifluoroacetic acid/dichloromethane.

SCHEME IV

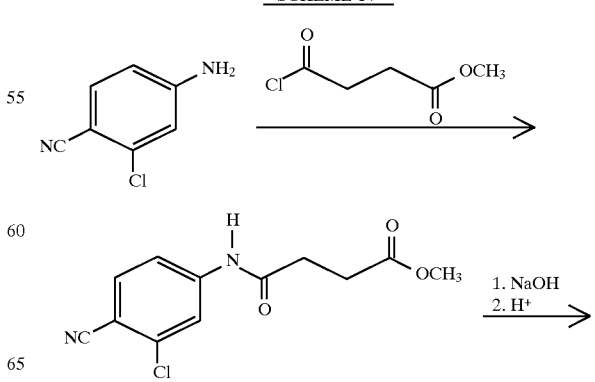

-continued
SCHEME IV
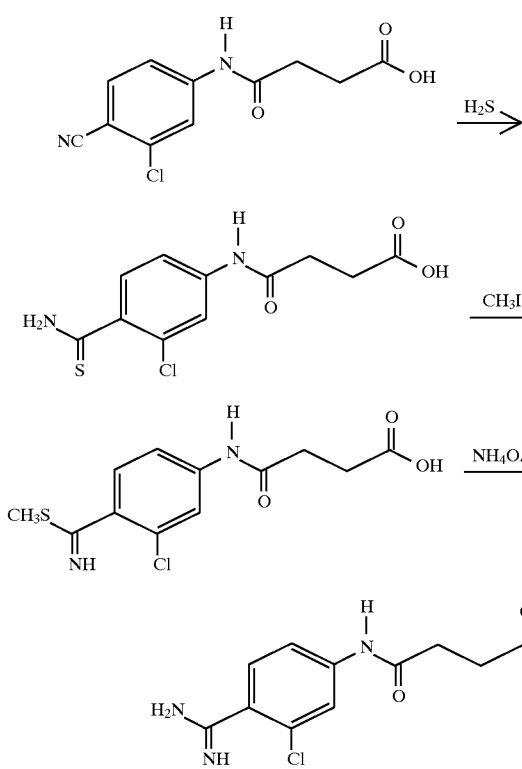
SCHEME V
Method 1
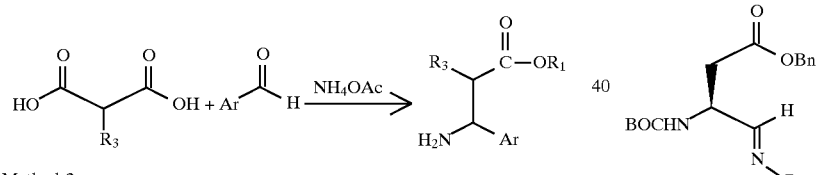
Method 2
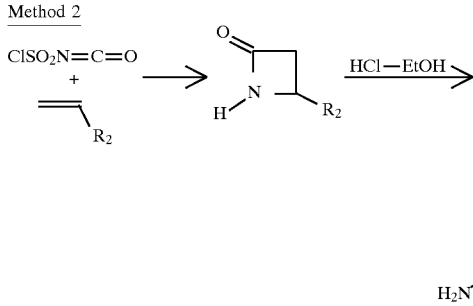
Method 3
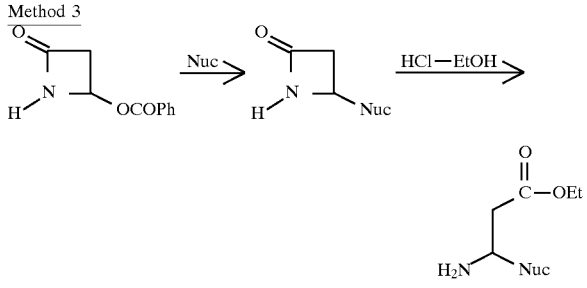
-continued
SCHEME V
Method 4
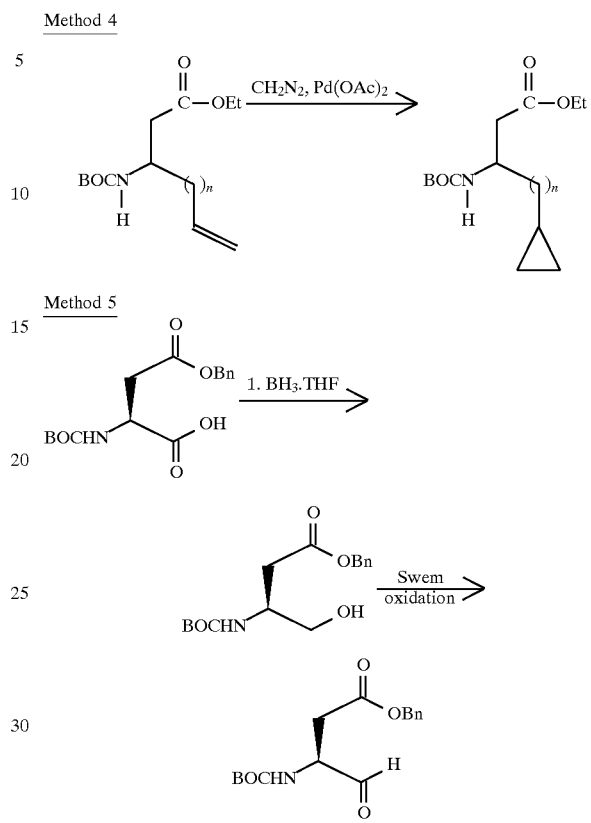
Method 5
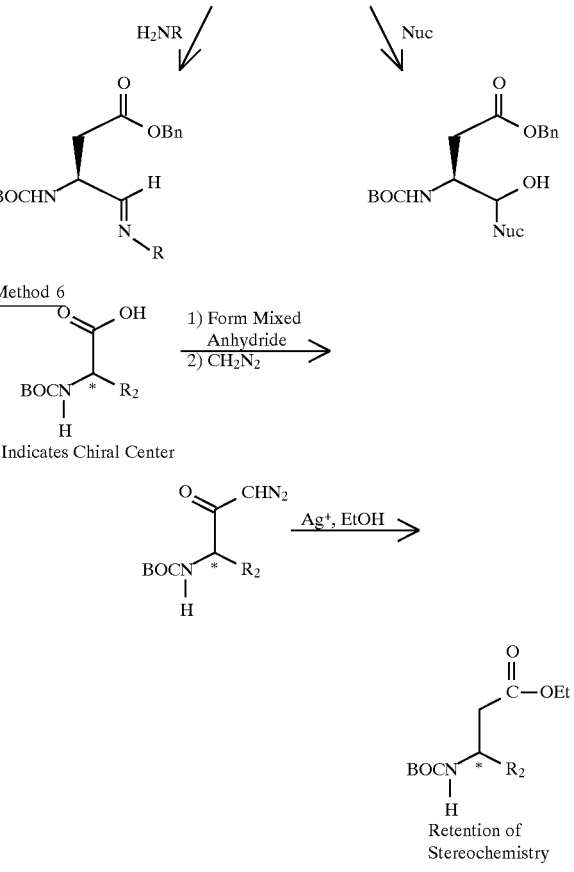

-continued
SCHEME V

Method 7

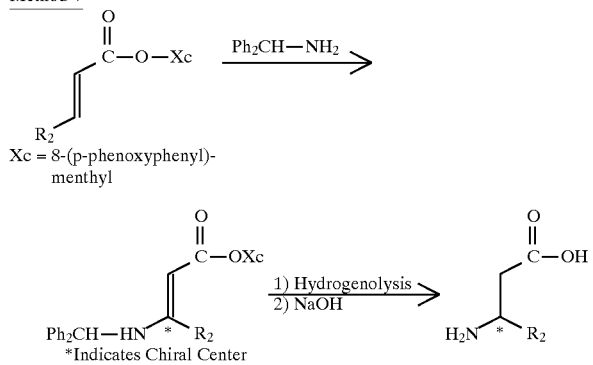

Xc = 8-(p-phenoxyphenyl)-menthyl

Method 8

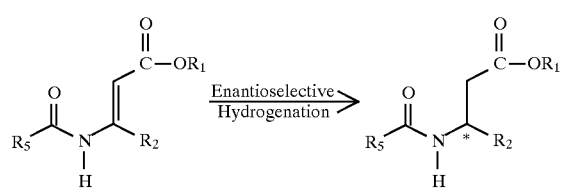

Method 9

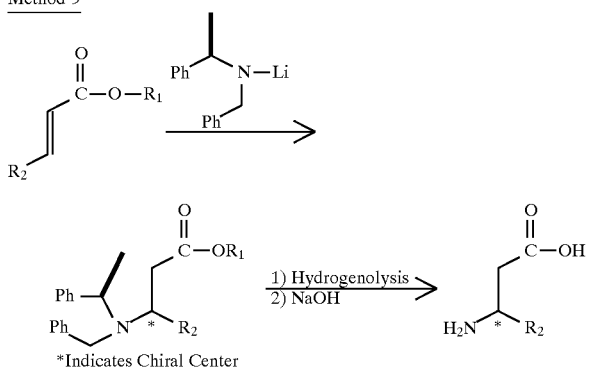

*Indicates Chiral Center

SCHEME IV and V. Substituted aminonitrile can be used to prepare substituted N-aminobenzamidine succinyl derivatives as specifically illustrated in Scheme IV for the chloro derivative 14. The beta amino acids can be either purchased or prepared from commercially available starting materials using known methods as illustrated in Scheme V. The racemic beta aryl beta amino acids can be prepared from the appropriate arylaldehyde, malonic acid, and ammonium acetate as shown in Scheme V—method 1 (Johnson and Livak *J. Am. Chem. Soc.* 299 (1936)]. The racemic beta alkyl beta amino acids can be prepared from the corresponding alkene and chlorosulfonyl isocyanate (CSI) which goes through the beta lactam intermediate as shown in Scheme V—method 2 [W. A. Szabo *Aldrichimica Acta* (1977); R. Graf *Angew. Chem. Internat. Edit.* 172 (1968)]. The beta lactam can be opened to the ethyl ester by treatment with anhydrous hydrochloric acid in ethanol as shown in Scheme V. For example, 1,3-butadiene and 3-phenyl-1-propene reacted with CSI forms the beta lactam which is subsequently followed by opening with anhydrous HCl in ethanol. An alternative method to form racemic beta amino esters is shown in Scheme V method 3. Nucleophiles can be added to 4-benzoyloxy-2-azetidinone to afford a variety of 3-substituted beta amino esters after treatment with anhydrous HCl in ethanol. For example, 1-lithio-2-trimethylsilylethyne is added to 4-benzoyloxy-2-azetidinone to afford a beta amino ester after ring opening [for a similar reaction see: D. H. Hua and A. Verma *Tetrahedron Lett.* 547–550 (1985) or T. Kametani, *Heterocycles* Vol. 17 463 (1982)]. As another example, 4-benzoyloxy-2-azetidinone was reacted with allyltrimethylsilane under Lewis acid catalysis [titanium tetrachloride-K. Prasad et al., Vol. 19 *Heterocycles* 2099 (1982)]. The cyclopropyl derivatives are prepared from the corresponding vinyl compounds by treatment with diazomethane and palladium acetate [U. Mande et al., *Tetrahedron Lett.* 629 (1975)] as shown in scheme V method 4. The racemic beta amino acids can be resolved using classical methods as described in the literature [E. Fischer, H. Scheibler, R. Groh *Ber.* 2020 (1910); E. Fischer, H. Scheibler *Annalen* 337 (1911)].

Chiral beta amino acids can be prepared using many different approaches including the following methods: homologation of the alpha amino acids using an Arndt-Eistert reaction as shown in Scheme V method 5 [Meier and Zeller *Angew. Chem. Int. Ed. Eng.* 32–43 (1975)] as shown in Scheme F method 3 [M. Rodriguez et al *Tetrahedron Lett.* 5153 (1990); W. J. Greenlee *J. Med. Chem.* 434 (1985) and references therein]; from enantiomerically pure precursors obtained from L-aspartic acid [i.e., Scheme V method 6, see: M. Rodriguez *Tetrahedron Lett.* 923 (1991)]; through the addition of chiral amines to alpha, beta unsaturated esters bearing a chiral auxiliary as shown in Scheme V method 7 [J. d'Angelo and J. Maddaluno *J. Am. Chem. Soc.* 8112–14 (1986)]; through an enantioselective hydrogenation of a dehydroamino acid as shown in Scheme V method 8 [see: Asymmetric Synthesis, Vol. 5, (J. D. Morrison, ed.) Academic Press, New York, 1985]; through the addition of enantiomerically pure amines to alpha, beta unsaturated esters as shown in Scheme V method 9 [see: S. G. Davies and O. Ichihara *Tetrahedron:Asymmetry* 183–186 (1991)].

Method 6 of Scheme V was used to obtain a versatile enantiomerically pure aldehyde intermediate. The aldehyde was reacted with methoxylamine to form an oxime. The appropriate organometallic was added to the aldehyde to afford the corresponding alcohol.

Purification of final compounds is by reverse phase high performance liquid chromatography (*High Performance Liquid Chromatography Protein and Peptide Chemistry*, F. Lottspeich, A. Henscher, K. P. Hupe, eds. Walter DeGruyter, New York, 1981, the disclosure of which is hereby incorporated by reference) or crystallization.

Contemplated equivalents of the general formulas set forth above for the platelet aggregation inhibitors and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

Either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees centigrade.

Within the foregoing synthetic description and examples which follow, abbreviations have the following meanings:

$CHCl_3$=chloroform

DMF=dimethylformamide

DMSO=dimethylsulfoxide g=gram

MeOH=methanol min=minute h=hour mol=mole mmol=mmole

MW=molecular weight

TLC=thin layer chromatography

NMM=N-methylmorpholine

RPHPLC=Reverse Phase High Performance Liquid Chromatography

TDA-1=Tris[2-(2-methoxyethoxy)ethyl]amine

PTC=Phase Transfer Catalysis mL=milliliter

EXAMPLE 1

Preparation of 4-[[4-(aminoiminomethyl)phenyl]-amino]-4-oxobutanoic acid

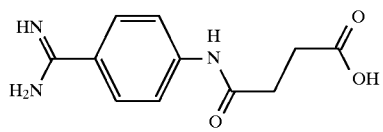

Aminobenzamidine di-HCl (25 g, 120 mmol), which is commercially available from Aldrich, was added to dry DMF (100 mL). To this was added dry pyridine (100 mL) and succinic anhydride (12 g, 120 mmol) followed by N,N-dimethylaminopyridine (DMAP, 0.15 g). The product precipitated after heating for 0.5 hour at 100° C. The product was filtered, washed with water, acetonitrile and ether. The white solid was suspended in dioxane, 4N HCl in dioxane (100 mL) was added and the suspension stirred for 1 hour, filtered and dried in a desiccator to give 28 g, 88% isolated yield of a yellowish-white solid whose nmr and mass spectra is consistent with 4-[[4-(aminoiminomethyl)phenyl)amino]-4-oxobutanoic acid HCl salt. Mp: 270°–290° C., decomp.

EXAMPLE 2

3S-[[[[4-(aminoiminomethyl)phenyl]amino]-1,4-dioxobutyl]amino]-4-(methoxymethylamino)-4-oxobutanoic acid

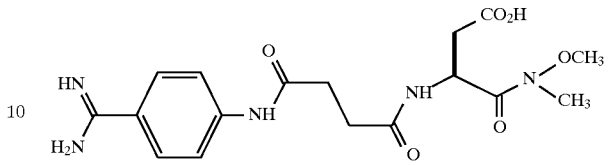

Step 1. Preparation of 3S-amino-4-(methoxymethylamino)-4-oxobutanoic acid

To N-tBoc-L-aspartic acid, beta-benzyl ester (10 g, 31 mmole) dissolved in 50 mL methylene chloride was added triethylamine (4.31 mL, 31 mmole). To this was added benzotriazol-1-yloxytris(dimethylamino)-phosphonium hexafluorophosphate (BOP) (10.8 g, 31 mmole). After several minutes O,N-dimethylhydroxyl amine hydrochloride (3.40 g, 33.5 mmole) and triethylamine (4.31 mL, 32.3 mmole) were added and the reaction allowed to proceed for several hours. The reaction mixture was diluted to 200 mL by addition of methylene chloride and washed successively with dilute aqueous hydrochloric acid, saturated aqueous sodium hydrogen carbonate, and saturated aqueous sodium chloride solution. The organic layer was dried with magnesium sulfate and volatiles removed in vacuo to give the crude product. This product was dissolved in ethyl acetate and passed over a 4×4 cm pad of Merck 60 silica gel. The ethyl acetate was evaporated to give 8.9 g of a product whose nmr and mass spec where consistent for desired product (78%).

The N-BOC amido benzyl ester prepared above (7.9 g, 21.6 mmole) was dissolved in 50 mL methanol. The solution was transferred along with 0.5 gm 3% palladium on carbon catalyst to a medium pressure hydrogenation apparatus equipped with a magnetic stirring bar, pressure gauge and gas inlet and outlet valves. Hydrogen was introduced (54 psig) and the reaction allowed to continue overnight. The catalyst was removed by filtration over a celite pad and the solvent removed in vacuo to give the desired N-BOC amido acid: $^1$H NMR (300 MHz, $d_6$DMSO); 1.45 (s, 9H), 2.8 (m, 2H), 3.20 (s, 3H), 3.72 (s, 3H), 4.55 (m, 1H). FABMS 283 (M+Li).

The N-BOC amido acid prepared above was dissolved in a minimum of 1,4-dioxane and 50 mL of 4N HCl in dioxane added at room temperature. The reaction was allowed to proceed until no further gas evolution was noted (30 minutes) and the solvent evaporated. The desired amino acid as the trifluoroacetate salt was isolated by preparative C-18 reverse-phase high-performance liquid chromatography (RPHPLC) and lyophilized to give a white powder (2.33 grams, 8 mmole, 38% overall isolated yield): $^1$H NMR (300 MHz, $d_6$ DMSO):3.02 (bs, 2H), 3.125 (s, 3H), 3.687 (s, 3H), 4.183 (m, 1H). FABMS 177.1 (M+H).

Step 2. Preparation of 3S-[[[[4-(aminoiminomethyl)-phenyl]amino]-1,4-dioxobutyl]amino]-4-(methoxymethylamino)-4-oxobutanoic acid.

Coupling of 3S-amino-4-(methoxymethylamino)-4-oxobutanoic acid to 4-[[4-(aminoiminomethyl)phenyl]-amino]-4-oxobutanoic acid was achieved in the following fashion. 4-[[4-(aminoiminomethyl)phenyl]amino]-4-oxobutanoic acid hydrochloride (0.70 g, 2.6 mmole) prepared in Example 1 was reacted with isobutylchloroformate (0.34 mL, 2.6 mmole) and an equivalent of N-methylmorpholine (0.29 mL, 2.6 mmole) in DMF. Following activation 3S-amino-4-(methoxymethylamino)-4-oxobutanoic acid (0.5 g, 1.7 mmole) was added with an equivalent of N-methylmorpholine and the reaction allowed to proceed overnight. The solvent was removed and the product isolated by preparative hplc and the fractions containing desired product taken to pH 6 with lithium hydroxide. The lithium salt was isolated by lyophilization. $^1$H NMR (300 MHz, $d_6$ DMSO): 2.65 (bm, 6H) 3.05, 3.10 (s, 3H), 3.65, 3.7 (s, 3H), 7.8 (m, 5H), 9.5 (bd, 4H), 10.6 (d, 1H). FABMS 394 (M+H), 400.3 (M+Li); HRFABMS.

EXAMPLE 3

N-[4-[[4-(aminoiminomethyl)phenyl]amino]-1,4-dioxobutyl]aspartic acid

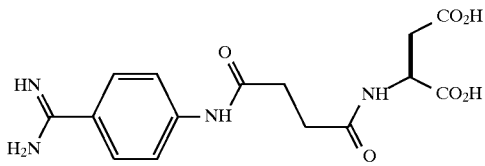

3S-[[[[4-(aminoiminomethyl)phenyl]amino]-1,4-dioxobutyl]amino]-4-(methoxymethylamino)-4-oxobutanoic acid (1.6 g) from Example 2 was taken up in 300 mL water made acidic (pH 2) with trifluoroacetic acid and heated at 60° C. for several hours. The product diacid-benzamidine was isolated by preparative RPHPLC and lyophilized to give the desired product (0.84 g). $^1$H NMR (300 MHz, $d_6$ DMSO):2.55 (bm, 6H), 4.5 (m, 1H), 7.8 (s, 4H), 8.2 (d, 1H), 9.15 (bs, 4H), 10.4 (d, 1H), FABMS 351.3 (M+H).

EXAMPLE 4

Preparation of N-[4-[[4-(aminoiminomethyl)phenyl]-amino]-1,4-dioxobutyl]aspartic acid, 4-(1,1-dimethylethyl)ester

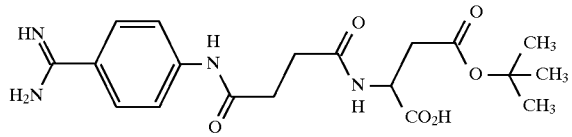

To a flame-dried flask under argon atmosphere, 4-[[4-(aminoiminomethyl)phenyl]amino]-5-oxopentanoic acid (2.0 g, 7.4 mmole) prepared in Example 1 is added to dry DMF and dry pyridine (1:1 v/v, 70 mL) followed by N-methylmorpholine (0.74 g, 7.4 mmole) and N,N'-disuccinimidyl carbonate, DSC (1.9 g, 7.4 mmole) along with DMAP (50 mg) at room temperature. Upon cessation of gas evolution a solution of L-aspartic acid beta-t-butyl ester (1.5 g, 8 mmol, obtained from BACHEM) in DMF:pyridine (1:1, 20 mLs) is added and the reaction allowed to proceed overnight. The solvent is removed at 55° C. under reduced pressure and the product is purified by preparative C-18 reverse-phase high-performance liquid chromatography, RPHPLC (gradient of water and 0.05% v/v trifluoroacetic acid (TFA) to water: TFA/acetonitrile and 0.05% v/v TFA) and lyophilized to give the desired product as a TFA salt.

EXAMPLE 5

Preparation of N-[4-[[4-(aminoiminomethyl)phenyl]-amino]-1,4-dioxobutyl]aspartic acid, 4-(phenylmethyl)ester

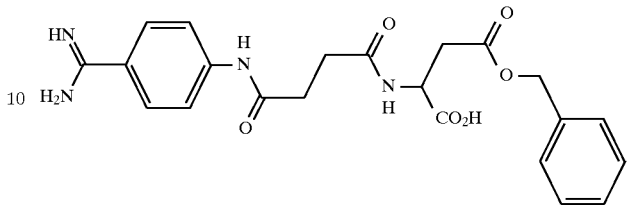

Preparation of N-[4-[[4-(aminoiminomethyl)-phenyl]amino]-1,4-dioxobutyl]aspartic acid, 4-(phenylmethyl)ester is achieved using the procedure of Example 4 but substituting L-aspartic acid beta-benzyl ester (1.8 g, 8 mmol, Fluka) for L-aspartic acid beta-t-butyl ester. The coupling reaction is allowed to proceed overnight, volatiles are removed under reduced pressure and the desired product is purified by rphplc and lyophilized to obtain substantially pure N-[4-[[4-(aminoiminomethyl)-phenyl]amino]-1,4-dioxobutyl] aspartic acid, 4-(phenylmethyl)ester.

EXAMPLE 6

Preparation of N-[4-[[4-(aminoiminomethyl)phenyl]-amino]-1,4-dioxobutyl]aspartic acid, 4-methyl ester

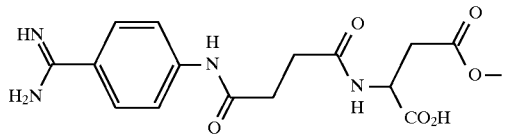

Preparation of N-[4-[[4-(aminoiminomethyl)phenyl]-amino]-1,4-dioxobutyl)aspartic acid, 4-methyl ester is achieved using the procedure of Example 4 but substituting L-aspartic acid beta-methyl ester (1.2 g, 8 mmol, Sigma) for L-aspartic acid beta-t-butyl ester. The coupling reaction is allowed to proceed overnight, volatiles are removed under reduced pressure and the desired product is purified by RPHPLC and lyophilized to obtain substantially pure N-[4-[[4-(aminoiminomethyl)phenyl]amino]-1,4-dioxobutyl] aspartic acid, 4-methyl ester.

EXAMPLE 7

Preparation of N-[4-[[4-(aminoiminomethyl)phenyl]-amino]-1,4-dioxobutyl]aspartic acid, 4-ethyl ester

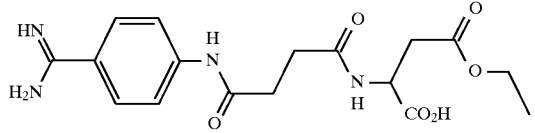

Preparation of N-[4-[[4-(aminoiminomethyl)phenyl]-amino]-1,4-dioxobutyl]aspartic acid, 4-ethyl ester is achieved using the procedure of Example 4 but substituting L-aspartic acid beta-ethyl ester hydrochloride (1.6 g, 8 mmol, Aldrich) for L-aspartic acid beta-t-butyl ester. The coupling reaction is allowed to proceed overnight, volatiles are removed under reduced pressure and the desired product is purified by RPHPLC and lyophilized to obtain substantially pure N-[4-[[4-(aminoiminomethyl)-phenyl]amino]-1,4-dioxobutyl]aspartic acid, 4-ethyl ester.

EXAMPLE 8

Preparation of N-[4-[[4-(aminoiminomethyl)phenyl]-amino]-1,4-dioxobutyl]aspartic acid, 4-(3-propenyl) ester

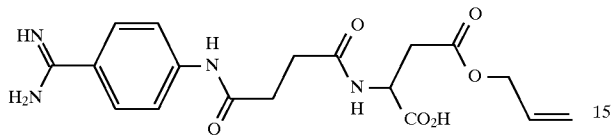

Preparation of N-[4-[[4-(aminoiminomethyl)phenyl]-amino]-1,4-dioxobutyl]aspartic acid, 4-(3-propenyl)ester is achieved using the procedure of Example 4 but substituting L-aspartic acid beta-allyl ester (1.4 g, 8 mmol) for L-aspartic acid beta-t-butyl ester. The coupling reaction is allowed to proceed overnight, volatiles are removed under reduced pressure and the desired product is purified by RPHPLC and lyophilized to obtain substantialily pure N-[4-[[4-(aminoiminomethyl)-phenyl]amino]-1,4-dioxobutyl] aspartic acid, 4-(3-propenyl)ester.

EXAMPLE 9

Preparation of N-[4-[[4-(aminoiminomethyl)phenyl]-amino]-1,4-dioxobutyl]aspartic acid, 1-(1,1-dimethylethyl)ester

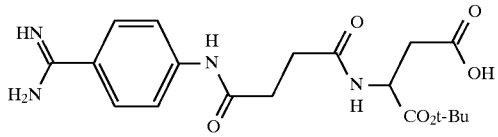

Preparation of N-[4-[[4-(aminoiminomethyl)phenyl]-amino]-1,4-dioxobutyl]aspartic acid, 1-(1,1-dimethylethyl) ester is achieved using the procedure of Example 4 but substituting L-aspartic acid alpha-t-butyl ester hydrochloride (1.8 g, 8 mmol, BACHEM or Nova Biochem) for L-aspartic acid beta-t-butyl ester. The coupling reaction is allowed to proceed overnight, volatiles are removed under reduced pressure and the desired product is purified by RPHPLC and lyophilized to obtain substantially pure N-[4-[[4-(aminoiminomethyl)phenyl]amino]-1,4-dioxobutyl]-aspartic acid, 1-(1,1-dimethylethyl)ester.

EXAMPLE 10

Preparation of N-[4-[[4-(aminoiminomethyl)phenyl]-amino]-1,4-dioxobutyl]aspartic acid, 1-phenylmethyl ester

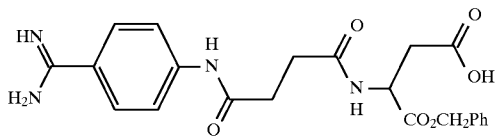

Preparation of N-[4-[[4-(aminoiminomethyl)phenyl]-amino]-1,4-dioxobutyl]aspartic acid, 1-phenylmethyl ester is achieved using the procedure of Example 4 but substituting L-aspartic acid alpha-benzyl ester hydrochloride (2.1 g, 8 mmol, BACHEM or Nova Biochem) for L-aspartic acid beta-t-butyl ester. The coupling reaction is allowed to proceed overnight, volatiles are removed under reduced pressure and the desired product is purified by RPHPLC and lyophilized to obtain substantially pure N-[4-[[4-(aminoiminomethyl)phenyl]amino]-1,4-dioxobutyl]aspartic acid, 1-phenylmethyl ester.

EXAMPLE 11

Dimethyl 3-[[4-[[4-(aminoiminomethyl)phenyl]-amino]-1,4-dioxobutyl]amino]pentanedioate

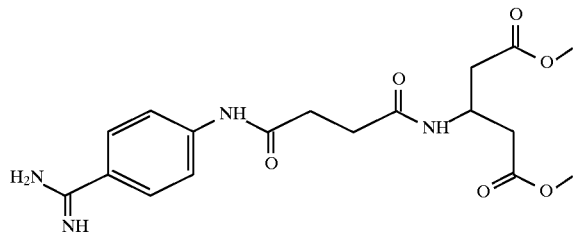

Step 1. Preparation of dimethyl-3-aminoglutarate

Dimethyl-3-oxoglutarate (10 g, 57 mmol) was added to methanol (225 ml) followed by ammonium formate (36 g, 570 mmol) and NaBH$_3$CN (3.7 g, 57 mmol) at 25° C. After 24 hours the methanol was removed in vacuo to leave a white mass. Methylene chloride was added and the mixture filtered. The methylene chloride was evaporated resulting in an oil which was dissolved in 1N HCl (200 ml) and extracted with ether (100 ml). The ether layer was discarded and the aqueous layer was made basic using solid K$_2$CO$_3$. The product was extracted into methylene chloride dried over Na$_2$SO$_4$ and evaporated to give dimethyl-3-aminoglutarate (7.5 g). $^1$H NMR (d$_6$-DMSO) δ 1.76 (bs, 2H), 2.45 (dd, 4H, J=8.08 Hz, 16.64 Hz), 3.69 (s, 6H), 5.45 (m, 1H); MS (FAB) m/e 176.0 (M+H+).

Step 2. Preparation of dimethyl 3-[[4-[[4-(aminoiminomethyl)phenyl]amino]-1,4-dioxobutyl]amino] pentanedioate 4-[[4-(aminoiminomethyl)phenyl]amino]-4-oxobutanoic acid hydrochloride prepared in Example 1 (4.6 g, 17 mmol) was added to dry DMF (225 ml) followed by N-methylmorpholine (1.2 g, 17 mmol) and isobutyl chloroformate (2.3 g, 17 mmol) at 25° C. The mixture was stirred for 5 minutes. Dimethyl-3-aminoglutarate (3.0 g, 17 mmol) was added followed by dimethylaminopyridine. After 1 hour the solvent was removed under reduced pressure and the product purified by reverse phase chromatography (water/acetonitrile) to result in 3.5 g of a white solid: $^1$H NMR (d$_6$-DMSO) δ 2.37 (t, 2H, J=7.3 Hz), 2.55 (m, 2H), 2.57 (t, 2H, J=7.1 Hz), 3.57 (s, 6H), 4.35 (m, 1H), 7.79 (s, 4H), 7.99 (d, Hz), 9.1 (bs, 2H), 9.19 (bs, 2H), 10.42 (s, 1H); MS (FAB) m/e 393.2 (M+H+).

Elemental Analysis Required for C$_{18}$H$_{24}$N$_4$O$_6$.F$_3$.C$_2$O$_2$H.H$_2$O: C, 47.42; H, 4.91; N, 11.14. Found: C, 47.12; H, 4.97; N, 10.99.

EXAMPLE 12

3-[[4-[[4-(aminoiminomethyl)phenyl]amino]-1,4-dioxobutyl]amino]pentanedioic acid, monomethylester

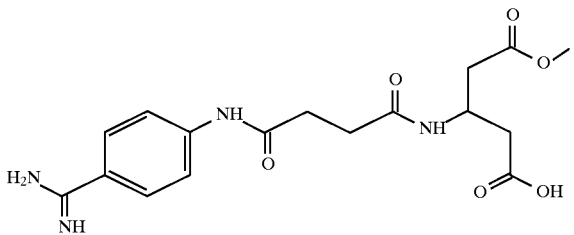

Dimethyl 3-[[4-[[4-(aminoiminomethyl)phenyl]amino]-1,4-dioxobutyl]amino]pentanedioate prepared in Example 11 (700 mg) was added to water/acetonitrile (20 ml) followed by lithium hydroxide (100 mg) at 25° C. The mixture was stirred for 30 minutes. The course of the reaction was monitored by RPHPLC. After satisfactory monoester was formed the reaction was neutralized with TFA and purified by reverse phase chromatography (water/acetonitrile) to result in 460 mg white solid: $^1$H NMR (d$_6$-DMSO) δ 2.39 (t, 2H, J=7.3 Hz), 2.55 (m, 2H), 2.57 (t, 2H, J=7.1 Hz), 3.57 (s, 3H), 4.32 (m, 1H), 7.78 (s, 4H), 7.99 (d, 1H, J=8.1 Hz), 8.92 (bs, 2H), 9.16 (bs, 2H), 10.39 (s, 1H); MS (FAB) m/e 379.2 (M+H+).

Elemental Analysis Required for $C_{17}H_{22}N_4O_6 \cdot F3 \cdot C_2O_2H \cdot H_2O$: C, 45.92; H, 4.63; N, 11.28. Found: C, 45.88; H, 4.34; N, 10.69.

EXAMPLE 13

(±)-Diethyl-3-[[4-[[4-(aminoiminomethyl)phenyl]-amino]-4-dioxobutyl]amino]heptanedioate

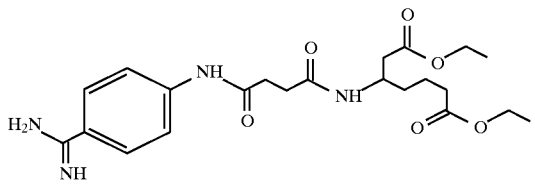

Step 1. Preparation of diethyl-3-aminopimaleate

Diethyl-3-oxopimaleate (10 g, 43 mmol) was added to methanol (225 ml) followed by ammonium formate (27.4 g, 430 mmol) and NaBH$_3$CN (2.7 g, 43 mmol) at 25° C. After 24 hours the methanol was removed in vacuo to leave a white mass. Methylene chloride was added and the mixture filtered. The methylene chloride was evaporated resulting in an oil which was dissolved in 1N HCl (200 ml) and extracted with ether (100 ml). The ether layer was discarded and the aqueous layer was made basic using solid K$_2$CO$_3$. The product was extracted into methylene chloride dried over Na$_2$SO$_4$ and evaporated to give diethyl-3-aminopimaleate (7.5 g). $^1$H NMR (d$_6$-DMSO) δ 1.25 (t, 3H, J=7 Hz), 1.26 (t, 3H, J=8 Hz), 1.45 (m, 2H), 1.7 (m, 2H), 2.01 (bs, 2H), 2.45 (m, 2H), 3.2 (m, 1H), 4.13 (q, 4H, J=8 Hz); MS (FAB) m/e 132.1 (M+H+) 186.2.

Step 2. Preparation of (±)-diethyl-3-[[4-[[4-(aminoiminomethyl)phenyl]amino]-1,4-dioxobutyl]-amino] heptanedioate

[[4-[[4-(Aminoiminomethyl)phenyl]amino]-4-oxobutanoic acid hydrochloride prepared in Example 1 (5.0 g, 18.5 mmol) was added to dry DMF (250 ml) followed by N-methylmorpholine (2.2 g, 18.5 mmol) and isobutyl chloroformate (2.7 g, 18.5 mmol) at 25° C. The mixture was stirred for 5 minutes. Diethyl-3-aminopimaleate (4.25 g, 18.5 mmol; from Step 1) was added followed by dimethylaminopyridine. After 1 hour, the solvent was removed under reduced pressure and the product purified by reverse phase chromatography (water/acetonitrile) to result in 4.1 g of a white solid: $^1$H NMR (d$_6$-DMSO) δ 1.15 (t, 3H, J=7.3 Hz), 1.16 (t, 3H, J=8 Hz), 1.4 (m, 2H), 2.50 (t, 2H, J=7.1 Hz), 2.49 (m, 4H), 2.58 (t, 2H, J=7.1 Hz), 4.04 (m, 5H), 7.78 (s, 4H), 7.79 (d, 1H, J=12.4 Hz), 8.95 (bs, 2H), 9.15 (bs, 2H), 10.40 (s, 1H), MS (FAB) m/e 449.0 (M+H+).

Elemental Analysis Required for $C_{22}H_{32}N_4O_6 \cdot F_3 \cdot C_2O_2H \cdot H_2O$: C, 50.44; H, 5.95; N, 9.80. Found: C, 50.33; H, 6.02; N, 9.67.

In-Vitro Platelet Aggregation in PRP

The platelet-binding for activity of the compounds of the present invention can be demonstrated by the assay described below.

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature allowing the centrifuge to coast to a stop without braking. The PRP was removed from the blood with a plastic pipette and placed in a plastic capped, 50 mL Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per mL. 400 uL of the PRP preparation and 50 uL of the compound to be tested in solution or saline were preincubated for 1 minute at 37° C. in an aggregometer (BioData, Horsham, Pa.). 50 uL of adenosine 5' diphosphate (ADP) (50 um final concentration) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline)]×100. The % inhibition=100−(percent of control).

IC$_{50}$'s (dosage at which 50% of platelet aggregation is inhibited) were calculated by linear regression of the dose response curve. The assay result for the compound of Example 3 was 4.8 μm.

What is claimed is:
1. A compound of the formula

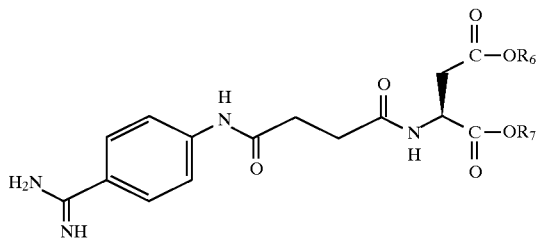

wherein R$_6$ and R$_7$ are independently selected from the group consisting of hydrogen, lower alkyl radicals, aromatic hydrocarbon radicals, alicyclic hydrocarbon radicals, and arylalkyl radicals wherein all of the radicals are optionally substituted.

2. A compound according to claim 1 wherein $R_6$ and $R_7$ are H.

3. A compound according to claim 1 wherein $R_7$ is H and $R_6$ is alkyl.

4. A compound according to claim 3 wherein $R_6$ is t-butyl.

5. A compound according to claim 3 wherein $R_6$ is methyl.

6. A compound according to claim 3 wherein $R_6$ is ethyl.

7. A compound according to claim 1 wherein $R_6$ is phenylmethyl and $R_7$ is H.

8. A compound according to claim 1 wherein $R_6$ is H and $R_7$ is t-butyl.

9. A compound according to claim 1 wherein $R_6$ is H and $R_7$ is benzyl.

10. A compound according to claim 1 wherein $R_7$ is t-butyl and $R_6$ is phenylmethyl.

11. A pharmaceutical composition comprising a therapeutically effective amount of a compound of the formula:

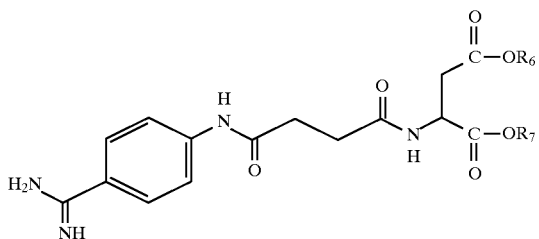

wherein $R_6$ and $R_7$ are independently selected from the group consisting of hydrogen, lower alkyl radicals, aromatic hydrocarbon radicals, alicyclic hydrocarbon radicals, and arylalkyl radicals wherein all of the radicals are optionally substituted; and
a pharmaceutically acceptable carrier.

12. A pharmaceutical composition according to claim 11 wherein the compound is selected from the group consisting of:

2S-[4-[[4-(aminoiminomethyl)phenyl]amino]-1,4-dioxobutyl]aspartic acid;

N-[4-[[4-(aminoiminomethyl)phenyl]amino]-1,4-dioxobutyl]aspartic acid, 4-(1,1-dimethylethyl)ester;

N-[4-[[4-(aminoiminomethyl)phenyl]amino]-1,4-dioxobutyl]aspartic acid, 4-(phenylmethyl)ester;

N-[4-[[4-(aminoiminomethyl)phenyl]amino]-1,4-dioxobutyl]aspartic acid, 4-methyl ester;

N-[4-[[4-(aminoiminomethyl)phenyl]amino]-1,4-dioxobutyl]aspartic acid, 4-ethyl ester;

N-[4-[[4-(aminoiminomethyl)phenyl]amino]-1,4-dioxobutyl]aspartic acid, 4-(3-propenyl)ester;

N-[4-[[4-(aminoiminomethyl)phenyl]amino]-1,4-dioxobutyl]aspartic acid, 1-(1,1-dimethylethyl)ester;

and

N-[4-[[4-(aminoiminomethyl)phenyl]amino]-1,4-dioxobutyl]aspartic acid, 1-phenylmethyl ester.

13. A method of inhibiting platelet aggregation in a mammal in need of such treatment comprising administering a therapeutically effective amount of a compound of the formula:

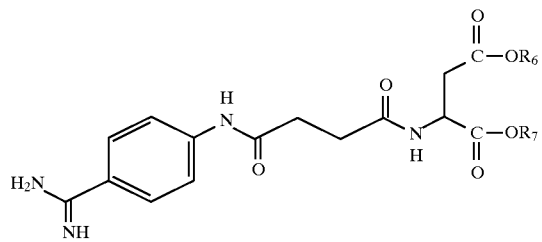

wherein $R_6$ and $R_7$ are independently selected from the group consisting of hydrogen, lower alkyl radicals, aromatic hydrocarbon radicals, alicyclic hydrocarbon radicals, and arylalkyl radicals wherein all of the radicals are optionally substituted.

14. A method according to claim 13 wherein the compound is selected from the group consisting of:

2S-[4-[[4-(aminoiminomethyl)phenyl]amino]-1,4-dioxobutyl]aspartic acid;

N-[4-[[4-(aminoiminomethyl)phenyl]amino]-1,4-dioxobutyl]aspartic acid, 4-(1,1-dimethylethyl)ester;

N-[4-[[4-(aminoiminomethyl)phenyl]amino]-1,4-dioxobutyl]aspartic acid, 4-(phenylmethyl)ester;

N-[4-[[4-(aminoiminomethyl)phenyl]amino]-1,4-dioxobutyl]aspartic acid, 4-methyl ester;

N-[4-[[4-(aminoiminomethyl)phenyl]amino]-1,4-dioxobutyl]aspartic acid, 4-ethyl ester;

N-[4-[[4-(aminoiminomethyl)phenyl]amino]-1,4-dioxobutyl]aspartic acid, 4-(3-propenyl)ester;

N-[4-[[4-(aminoiminomethyl)phenyl]amino]-1,4-dioxobutyl]aspartic acid, 1-(1,1-dimethylethyl)ester;

and

N-[4-[[4-(aminoiminomethyl)phenyl]amino]-1,4-dioxobutyl]aspartic acid, 1-phenylmethyl ester.

* * * * *